United States Patent [19]

Cook

[11] Patent Number: 5,180,729
[45] Date of Patent: Jan. 19, 1993

[54] USE OF SIGMA RECEPTOR ANTAGONISTS FOR TREATMENT OF COCAINE ABUSE

[75] Inventor: Leonard Cook, Newark, Del.

[73] Assignee: Du Pont Merck Pharmaceutical Company, Wilmington, Del.

[21] Appl. No.: 659,444

[22] Filed: Feb. 22, 1991

[51] Int. Cl.$^5$ ............... A61K 31/445; A61K 31/505; A61K 31/44; A61K 31/21

[52] U.S. Cl. ................................. 514/317; 514/256; 514/306; 514/314; 514/318; 514/323; 514/326; 514/415; 514/419

[58] Field of Search ............... 514/332, 256, 306, 314, 514/317, 318, 323, 326, 415, 419

[56] References Cited

PUBLICATIONS

Sharkey, J. et al, Eur J Pharmacol 149(1-2): 171-174 Mar. 1988.
Schlemmer et al., Soc. Neurosci. Abstr. 12(1):480 (1986).
Taylor et al., Drug Development Research 11:65-70 (1987).
Snyder et al., J. Neuropsychiatry 1:7-15 (1989).
Kosten, J. Nervous and Mental Disease 177:379-389 (1989).
Hock et al., Drug Development Research 6:301-311 (1985).
Ferris et al., Life Sciences 38:2329-2337 (1986).
Ogren et al., Eur. J. Pharmacology 102:459-474 (1984).
Kuhar et al. (1988) NIDA Monograph 88: 14-21.

*Primary Examiner*—Frederick E. Waddell
*Assistant Examiner*—Diane Gardner
*Attorney, Agent, or Firm*—Blair Q. Ferguson

[57] ABSTRACT

The invention relates to a method of treating cocaine abuse or addiction in a mammal which comprises administering to the mammal an effective amount of a sigma receptor antagonist lacking or having relatively weak dopamine receptor-blocking activity, to reduce the pharmacological effects of the cocaine.

33 Claims, 2 Drawing Sheets

USE OF SIGMA RECEPTOR ANTAGONISTS FOR TREATMENT OF COCAINE ABUSE

BACKGROUND OF THE INVENTION

Cocaine abuse has become a major public health problem in the United States, with over 20 million abusers in 1989. The quantity and frequency of cocaine use is increased markedly in the "recreational" cocaine user who switches to the high-intensity routes of cocaine administration, such as intravenous or free-base smoking. This high-intensity transition may lead to neurochemical and functional changes in the brain (Kosten (1989) J. Nervous and Mental Disease 177: 379–389). There is, therefore, presently an urgent need for improved methods of treatment for drug abuse involving cocaine. In addition to purely psychological treatments for helping cocaine abusers, there is a need for pharmacological treatments, especially for severe intravenous and free-base cocaine abusers.

Cocaine is reported to exert at least some of its pharmacological effects via the dopaminergic system. Chronic cocaine use in animals induces changes and increased sensitivity in postsynaptic dopaminergic receptors (Kosten (1989) J. Nervous and Mental Disease 177: 379–389).

Neuroleptic drugs, which are the primary antipsychotic drugs used in the treatment of schizophrenia, have been suggested for pharmacotherapy to treat psychotic symptoms during the early phase of withdrawal and recovery from cocaine abuse (Kosten (1989) J. Nervous and Mental Disease 177: 379–389). Such neuroleptics exert their therapeutic effects by binding to and blocking dopamine receptors, primarily $D_2$ receptors (Snyder and Largent (1989) J. Neuropsychiatry 1: 7–15). Some neuroleptics, such as cinuperone, tiospirone, and haloperidol, are known to nonselectively antagonize both sigma and dopamine $D_2$ receptors (Snyder and Largent (1989) J. Neuropsychiatry 1: 7–15).

SUMMARY OF THE INVENTION

In the present invention, sigma receptor antagonists lacking or having relatively weak dopamine receptor-blocking activity were discovered to reduce and counteract the pharmacological effects of cocaine in a mammal. By "sigma receptor antagonists lacking or having relatively weak dopamine receptor-blocking activity" we mean compounds having an inhibition constant, $K_i$, of 500 nM or less for sigma receptors and having at least a 5-fold greater affinity for sigma receptors relative to dopamine receptors. The sigma receptor antagonists useful in the present invention preferably have a $K_i$ for sigma receptors of less than 100 nM and at least a 50 to 100-fold greater affinity for sigma receptors than for dopamine receptors.

Unlike neuroleptics, the sigma receptor antagonists useful in the method of the present invention lack or have relatively weak dopamine receptor-blocking activity. Thus, the sigma receptor antagonists useful in the present invention, unlike neuroleptics, elicit their effects without directly antagonizing the dopamine receptor system.

The present invention provides a method of treating drug abuse or addiction in a mammal, involving cocaine and cocaine-related drugs exhibiting similar pharmacologial effects as cocaine, by administering to the mammal an effective amount of a sigma receptor antagonist lacking or having weak dopamine receptor-blocking activity. Cocaine abuse treated by the method of the present invention includes treatment following a single ingestion of cocaine.

The sigma receptor antagonist compounds useful in this invention include (N-phthalimidoalkyl) piperidines of the formula:

or a pharmaceutically acceptable salt or an N-oxide thereof wherein:

a is a single or double bond, provided that when a is a double bond then $R^2(CH_2)n$ is attached at C-4;

n is 0–4, provided that when $(CH_2)_nR^2$ is attached to the 2-position of the piperidine ring then n is 2–4;

$R^1$ is $(CH_2)_mR^3$ or $(CH_2)_pAr$, where m is 1–4 and p is 1–4;

$R^2$ is

-continued

-continued $R^3$ is cycloalkyl of 3 to 8 carbon atoms;

$R^4$ is 1–4 substituents independently selected from the group consisting of H, halogen, $NO_2$, $NH_2$, haloalkyl of 1 to 3 carbon atoms and 1 to 7 halogen atoms, $C_1$–$C_3$ alkyl, $NHCOR^7$, NHCO-phenyl, OH, $OR^8$ and AR';

$R^5$ and $R^6$ independently are H, alkyl of 1 to 3 carbon atoms, Ar" or taken together are —CH=CH—CH=CH—;

$R^7$ and $R^8$ independently are H or alkyl of 1 to 3 carbon atoms;

X is O; $H_2$; H, OH; $R^9$, OH; Ar'", OH; H, $R^9$; or H, $OR^9$;

Y is $CH_2$, $CHR^{10}$, $C(R^{10})_2$, O, $CH_2CH_2$, $(CH_2)_3$, $$\overset{\diagup}{\underset{S}{A}}, \quad \square \quad \text{or} \quad \square;$$

Ar, Ar', Ar" and Ar'" independently are phenyl optionally substituted with 1–5 substituents independently selected from the group consisting of: H, halogne, OH, alkoxy of 1 to 3 carbon atoms, of $NR^{11}R^{12}$, SH, $S(O)_tR^{13}$, where t is 0-2, haloalkyl 1 to 3 carbon atoms and 1 to 7 halogen atoms, alkyl of 1 to 3 carbon atoms, $CO_2H$, carboalkoxy of 2 to 6 carbon atoms, CN, $NO_2$, $SO_2NH_2$, $SO_3H$, $CO_2NR^{14}R^{15}$, naphthyl, pyridyl, pyrimidyl, quinolyl or isoquinolyl;

$R^9$ and $R^{10}$ independently are alkyl of 1 to 3 carbon atoms;

$R^{11}$–$R^{15}$ independently are H or alkyl of 1 to 3 carbon atoms;

$R^{16}$ is H; OH; O-alkyl of 1-6 carbons; O-acyl of 1-8 carbons; alkyl of 1-12 carbons; phenyl substituted with one or two substituents independently selected from F, Cl, Br, I, alkyl, perfluoroalkyl, alkoxy, arylosy, alkylthio, arylthio, perfluoroalkoxy, perfluoroalkylthio, and dialkylamino (alkyl and alkoxy 1-12 carbons; aryl 6-12 carbons); 1- and 2-naphthyl substituted with one or two substituents independently selected from F, Cl, Br, I, alkyl, perfluoroalkyl, alkoxy, arylosy, alkylthio, arylthio, perfluoroalkoxy, perfluoroakylthio, and dialkylamino (alkyl and alkoxy 1-12 carbons; aryl 6-12 carbons); 2- and 3-pyrrolyl; 2- and 3- furyl; 2- and 3- thienyl; 2,3, and 4-pyridyl; 2- and 3-benzolfuryl; 2- and 3- indolyl; 2- and 3-benzothienyl; 2, 3, and 4- quinolyl; and 1, 3, and 4-isoquinolyl;

with the following provisos:
(1) when $R^1$ is $(CH_2)_pAr$ (where p is 1);
$R^2$ is and
$(CH_2)_nR^2$, (n=O), is attached at the C-4 position on the piperidine ring; then X cannot be $H_2$ or O.
(2) $R^{16}$ is H, OH, alkyl or aryl when $(CH_2)n$ $R^2$ is attached to the 4-position of the piperidine ring.

Some compounds useful in the present invention can exist as optical isomers and both the racemic mixtures of these isomers as well as the individual optical isomers which confer activity are within the scope of compounds useful in the present invention.

In addition some compounds useful in the present invention can exist as cis or trans isomers and although these are not all specifically set forth, the cis and trans fused compounds as known to those skilled in the art, are within the scope of this invention.

Preferred compounds useful in the method of the present invention are compounds of Formula (I) for which one or more of the following occur:
n is 1-4;
$R^1$ is $(CH_2)_pAr$;
p is 1-2;
$R^2$ is $(CH_2)_nR^2$ is attached at the C-4 position of the piperidine ring;
X is O or $H_2$;
$R^4$, $R^5$ and $R^6$ are all H;
Ar is phenyl; or
Y is $(CH_2)_3$ or O.

More preferred compounds useful in the present invention are the compounds of formula (I) wherein n is 1.

The selective sigma receptor antagonist compounds useful in the present invention also include cycloalkylpiperidines of the formula:

$$\text{Ar}-(\text{C})_m\overset{R^1}{\underset{R^2}{|}}-X-(\text{C})_n\overset{R^3}{\underset{R^4}{|}}\overset{a}{\underset{b}{=}}\left(\begin{array}{c}\\ \\ \end{array}\right)N-(CH_2)_p-\triangleleft-R^5 \quad (II)$$

or a pharmaceutically acceptable salt thereof, wherein:
m is 0 to 3;
n is 0 to 3;
provided that m and n are not both 0;
p is 0 to 3;
X is O, S, SO, $SO_2$, $NR^6$, $CR^7R^8$, $$\overset{O}{\underset{C}{\|}},$$

or CHOH;
$R^1$, $R^3$ and $R^7$ independently are H, alkyl of 1 to 5 carbon atoms, halogen, $NR^{10}R^{11}$, OH, $CO_2H$, carboalkoxy of 2 to 6 carbon atoms, CN, $Ar^1$, alkoxy of 1 to 5 carbon atoms or alkylthio of 1 to 5 carbon atoms;
$R^2$, $R^4$ and $R^8$ independently are H, alkyl of 1 to 5 carbon atoms, carboalkoxy of 2 to 6 carbon atoms, CN, alkoxy of 1 to 5 carbon atoms or $Ar^1$;
provided that $R^1$, $R^2$, $R^3$ and $R^4$ are not alkoxy of 1 to 5 carbon atoms, alkylthio of 1 to 5 carbon atoms, $NR^{10}R^{11}$ or OH when X is O, S, SO, $SO_2$ or $NR^6$;

$R^5$ is H, alkyl, halogen, OH or alkenyl;

$R^6$ is H, alkyl of 1 to 5 carbon atoms or $Ar^1$

Ar and $Ar^1$ independently are naphthyl, pyridyl, pyrimidyl, indolyl, quinolinyl, isoquinolinyl, or phenyl optionally substituted with alkyl of 1 to 3 carbon atoms, alkoxy of 1 to 3 carbon atoms, haloalkyl of 1 to 3 carbon atoms and 1 to 7 halogen atoms, SH, $S(O)_t$ alkyl of 1 to 3 carbon atoms, where t is 1, 2 or 3, dialkylamino of 2 to 6 carbon atoms, halogen, OH, alkylamino of 1 to 3 carbon atoms, $NH_2$, CN, $NO_2$, $SO_3H$, tetrazole, $CO_2H$, carboalkoxy of 2 to 6 carbon atoms, $CONH_2$, $SO_2NH_2$, $COR^9$, $CONR^{12}R^{13}$, $SO_2NR^{12}R^{13}$, $Ar^2$, $OAr^2$ or $SAr^2$;

$Ar^2$ is naphthyl or phenyl optionally substituted with alkyl of 1 to 3 carbon atoms, haloalkyl of 1 to 3 carbon atoms and 1 to 7 halogen atoms, alkoxy of 1 to 3 carbon atoms, halogen or alkylthio of 1 to 3 carbon atoms;

$R^9$, $R^{10}$, $R^{11}$, $R^{12}$ and $R^{13}$ independently are H, alkyl of 1 to 5 carbon atoms or phenyl or $R^{10}$ and $R^{11}$ taken together are an alkylene chain of 3 to 6 carbon atoms or $R^{12}$ and $R^{13}$ taken together are an alkylene chain of 3 to 6 carbon atoms; and a or b is a double bond or a single bond, provided that both are not double bonds.

Preferred compounds useful in the present invention include those compounds of Formula (II) wherein:

X is C(O), CHOH or O;

m is 0;

n and p are 1;

$R^3$–$R^5$ are H; and/or

Ar is phenyl optionally substituted with halogen, $OCH_3$, $NH_2$, $NO_2$ or another phenyl group.

Pharmaceutical compositions comprising an effective amount of a compound of Formula I or II and a pharmaceutically acceptable carrier are useful in the method of the present invention.

Other sigma receptor antagonists lacking or having relatively weak dopamine receptor-blocking activity are expected to have similar medical and social benefits for the treatment of cocaine according to the present invention. Examples of other sigma receptor antagonists lacking or having weak domamine receptor-blocking activity and expected to be useful for the treatment of cocaine abuse are rimcazole (also known as BW234U) (Ferris et al. (1982) J. Pharm. Pharmacol. 34: 388–390; Ferris et al. (1986) Life Sciences 38: 2329–2337; U.S. Pat. No. 4,400,383; U.S. Pat. No. 4,588,728), remoxipride (Ogren et al. (1984) European Journal of Pharmacology 102: 439–474; U.S. Pat. No. 4,232,037; Snyder and Largent (1989) J. Neuropsychiatry 1: 7–15), and BMY14802 (Taylor and Dekleva (1987) Drug Development Research 11: 65–70; U.S. Pat. No. 4,605,655). The above identified patents are hereby incorporated by reference.

Other sigma receptor antagonists lacking or having relatively weak dopamine receptor-blocking activity and expected to be useful in the method of the invention include the compounds claimed in copending, commonly assigned U.S. patent applications U.S. Ser. No. 07/506961, filed 3/28/90 and U.S. Ser. No. 07/500573, filed 3/28/90, the disclosures of which are hereby incorporated by reference.

DETAILED DESCRIPTION OF THE INVENTION

We have discovered that sigma receptor antagonists lacking or having relatively weak dopamine receptor-blocking activity are useful to reduce and counteract the pharmacological effects of cocaine or cocaine-related drugs having similar pharmacological effects as cocaine in a mammal. We have found that agents which selectively block sigma receptors without directly blocking dopamine receptors are able to selectively ameliorate or inhibit cocaine-induced increases in motor activity, without inhibiting baseline motor activity (i.e., motor activity in the absence of cocaine).

The present invention provides a method of treating drug abuse or addiction in a mammal involving cocaine, by administering to the mammal an effective amount of a sigma receptor antagonist lacking or having weak dopamine receptor-blocking activity. Cocaine abuse treated by the method of the present invention includes treatment following a single ingestion of cocaine.

In the present invention, sigma receptor antagonists lacking or having relatively weak dopamine receptor-blocking activity were discovered to reduce and counteract the pharmacological effects of cocaine in a mammal. By "sigma receptor antagonists lacking or having relatively weak dopamine receptor-blocking activity" we mean compounds having an inhibition constant, $K_i$, of 500 nM or less for sigma receptors and having at least a 5-fold greater affinity for sigma receptors relative to dopamine receptors. The sigma receptor antagonists useful in the present invention preferably have a $K_i$ for sigma receptors of less than 100 nM and at least a 50 to 100-fold greater affinity for sigma receptors than for dopamine receptors.

Unlike neuroleptics, the sigma receptor antagonists useful in the method of the present invention lack or have relatively weak dopamine receptor-blocking activity. Thus, the sigma receptor antagonists useful in the present invention, unlike neuroleptics, elicit their effects without directly antagonizing the dopamine receptor system.

The sigma receptor antagonists useful in the present invention have weak affinity for dopamine receptors relative to their affinity for sigma receptors. We have discovered that such selective sigma receptor antagonists are able to selectively antagonize the effects of cocaine in an animal. In both rat and mouse animal models, it was found that a representative sigma receptor antagonist having weak dopamine receptor-blocking activity selectively antagonized the cocaine-induced behavior (cocaine-increased motor activity) without any significant depression in the normal baseline motor activity in animals in the absence of cocaine. This important and unexpected finding suggests that sigma receptor antagonists having weak dopamine receptor-blocking activity will effectively antagonize and attenuate the pharmacological effects of cocaine in humans at doses which will not have significant undesirable neurotoxic or adverse neurological effects.

The selective antagonism and attenuation of the pharmacological effects of cocaine by sigma receptor antagonists having weak dopamine receptor-blocking activity contrasts with the effect of dopamine receptor-blocking neuroleptics, such as haloperidol. Haloperidol causes an adverse non-selective attenuation of normal motor activity in cocaine-free animals at the same concentrations required to inhibit cocaine-induced motor activity. Thus, the sigma receptor antagonists having weak dopamine receptor-blocking activity show a substantial and unexpected advantage over dopamine receptor-blocking neuroleptics in the treatment of cocaine abuse.

The sigma receptor antagonist compounds useful in this invention include (N-phthalimidoalkyl) piperidines of the formula:

(I)

or a pharmaceutically acceptable salt or an N-oxide thereof wherein:

a is a single or double bond, provided that when a is a double bond then $R^2(CH_2)n$ is attached at C-4;

n is 0-4, provided that when $(CH_2)_nR^2$ is attached to the 2-position of the piperidine ring then n is 2-4;

$R^1$ is $(CH_2)_mR^3$ or $(CH_2)_pAr$, where m is 1-4 and p is 1-4;

$R^2$ is $R^3$ is cycloalkyl of 3 to 8 carbon atoms;

$R^4$ is 1–4 substituents independently selected from the group consisting of H, halogen, $NO_2$, $NH_2$, haloalkyl of 1 to 3 carbon atoms and 1 to 7 halogen atoms, $C_1$–$C_3$ alkyl, $NHCOR^7$, NHCO-phenyl, OH, $OR^8$ and Ar';

$R^5$ and $R^6$ independently are H, alkyl of 1 to 3 carbon atoms, Ar'' or taken together are —CH=CH—CH=CH—;

$R^7$ and $R^8$ independently are H or alkyl of 1 to 3 carbon atoms;

X is O; $H_2$, OH; $R^9$, OH; Ar''', OH; H, $R^9$; or H, $OR^9$;

Y is $CH_2$, $CHR^{10}$, $C(R^{10})_2$, O, $CH_2CH_2$, $(CH_2)_3$,

Ar, Ar', Ar'' and Ar''' independently are phenyl optionally substituted with 1–5 substituents independently selected from the group consisting of: H, halogen, OH, alkoxy of 1 to 3 carbon atoms, $NR^{11}R^{12}$, SH, $S(O)_tR^{13}$, where t is 0-2, haloalkyl of 1 to 3 carbon atoms and 1 to 7 halogen atoms, alkyl of 1 to 3 carbon atoms, $CO_2H$, carboalkoxy of 2 to 6 carbon atoms, CN, $NO_2$, $SO_2NH_2$, $SO_3H$, $CO_2NR^{14}R^{15}$, naphthyl, pyridyl, pyrimidyl, quinolyl or isoquinolyl;

$R^9$ and $R^{10}$ independently are alkyl of 1 to 3 carbon atoms;

$R^{11}$–$R^{15}$ independently are H or alkyl of 1 to 3 carbon atoms;

$R^{16}$ is H; OH; O-alkyl of 1–6 carbons; O-acyl of 1–8 carbons; alkyl of 1–12 carbons; phenyl substituted with one or two substituents independently selected from F, Cl, Br, I, alkyl, perfluoroalkyl, alkoxy, arylosy, alkylthio, arylthio, perfluoroalkoxy, perfluoroalkylthio, and dialkylamino (alkyl and alkoxy 1–12 carbons; aryl 6-12 carbons); 1- and 2-naphthyl substituted with one or two substituents independently selected from F, Cl, Br, I, alkyl, perfluoroalkyl, alkoxy, arylosy, alkylthio, arylthio, perfluoroalkoxy, perfluoroalkylthio, and dialkylamino (alkyl and alkoxy 1–12 carbons; aryl -12 carbons); 2- and 3-pyrrolyl; 2- and 3- furyl; - and 3- thienyl; 2,3, and 4-pyridyl; 2- and 3-benzolfuryl; 2- and 3- indolyl; 2- and 3-benzothienyl; 2, 3, and 4- quinolyl; and 1, 3, and 4-isoquinolyl;

with the following provisos:

(1) when $R^1$ is $(CH_2)_pAr$ (where p is 1); $R^2$ is and $(CH_2)_nR^2$, (n=0), is attached at the C-4 position on the piperidine ring; then X cannot be $H_2$ or O.

(2) $R^{16}$ is H, OH, alkyl or aryl when $(CH_2)_n R^2$ is attached to the 4-position of the piperidine ring.

Preferred compounds useful in the method of the present invention are compounds of Formula (I) for which one or more of the following occur;

n is 1-4;

$R^1$ is $(CH_2)_pAr$;

p is 1-2;

$R^2$ is or

$(CH_2)_nR^2$ is attached at the C-4 position of the piperidine ring;
X is O or $H_2$;
$R^4$, $R^5$ and $R^6$ are all H;
Ar is phenyl; or
Y is $(CH_2)_3$ or O.

More preferred compounds useful in the present invention are the compounds of formula (I) wherein n is 1.

Specifically preferred compounds useful in the present invention are compounds of formula (I) wherein:
(1) $(CH_2)_nR^2$ is attached at the C-4 position of the piperidine ring;
n is 1;
$R^2$ is

X is O;
$R^4$ is H;
$R^1$ is $(CH_2)_p$ Ar;
p is 2; and
Ar is phenyl.
(2) $(CH_2)_nR^2$ is attached at the C-4 position of the piperidine ring;
n is 1;
$R^2$ is X is O;
Y is $(CH_2)_3$ and $R^5$ and $R^6$ are H;
$R^1$ is $(CH_2)_pAr$;
p is 2; and
Ar is phenyl.
(3) $(CH_2)_nR^2$ is attached at the C-4 position of the piperidine ring;
n is 1;
$R^2$ is X is O;
Y is O;
$R^5$ and $R^6$ are H;
$R^1$ is $(CH_2)_pAr$;
p is 2; and
Ar is phenyl.
(4) $(CH_2)_nR^2$ is attached at the C-4 position of the piperidine ring;
n is 1;
$R^2$ is X is $H_2$;
$R^4$ is H;
$R^1$ is $(CH_2)_pAr$;
p is 2; and
Ar is phenyl.

The selective sigma receptor antagonist compounds useful in the present invention also include cycloalkyl-piperidines of the formula:

(II)

or a pharmaceutically acceptable salt thereof, wherein;
m is 0 to 3;
n is 0 to 3;
provided that m and n are not both O;
p is 0 to 3;
X is O, S, SO, $SO_2$, $NR^6$, $CR^7R^8$, or CHOH;
$R^1$, $R^3$ and $R^7$ independently are H, alkyl of 1 to 5 carbon atoms, halogen, $NR^{10}R^{11}$, OH, $CO_2H$, carboalkoxy of 2 to 6 carbon atoms, CN, $Ar^1$, alkoxy of 1 to 5 carbon atoms or alkylthio of 1 to 5 carbon atoms;
$R^2$, $R^4$ and $R^8$ independently are H, alkyl of 1 to 5 carbon atoms, carboalkyoxy of 2 to 6 carbon atoms, CN, alkoxy of 1 to 5 carbon atoms or $Ar^1$;
provided that $R^1$, $R^2$, $R^3$ and $R^4$ are not alkoxy of 1 to 5 carbon atoms, alkylthio of 1 to 5 carbon atoms, $NR^{10}R^{11}$ or OH when X is O, S, SO, $SO_2$ or $NR^6$;
$R^5$ is H, alkyl, halogen, OH or alkenyl;
$R^6$ is H, alkyl of 1 to 5 carbon atoms or $Ar^1$;

Ar and $Ar^1$ independently are naphthyl, pyridyl, pyrimidyl, indolyl, quinolinyl, isoquinolinyl, or phenyl optionally substituted with alkyl of 1 to 3 carbon atoms, alkoxy of 1 to 3 carbon atoms, haloalkyl of 1 to 3 carbon atoms and 1 to 7 halogen atoms, SH, $S(O)_t$ alkyl of 1 to 3 carbon atoms, where t is 1, 2 or 3, dialkylamino of 2 to 6 carbon atoms, halogen, OH, alkylamino of 1 to 3 carbon atoms, $NH_2$, CN, $NO_2$, $SO_3H$, tetrazole, $CO_2H$, carboalkoxy of 2 to 6 carbon atoms, $CONH_2$, $SO_2NH_2$, $COR^9$, $CONR^{12}R^{13}$, $SO_2NR^{12}R^{13}$, $Ar^2$, $OAr^2$ or $SAr^2$;

$Ar^2$ is naphthyl or phenyl optionally substituted with alkyl of 1 to 3 carbon atoms, haloalkyl of 1 to 3 carbon atoms and 1 to 7 halogen atoms, alkoxy of 1 to 3 carbon atoms, halogen or alkylthio of 1 to 3 carbon atoms;

$R^9$, $R^{10}$, $R^{11}$, $R^{12}$ and $R^{13}$ independently are H, alkyl of 1 to 5 carbon atoms or phenyl or $R^{10}$ and $R^{11}$ taken together are an alkylene chain of 3 to 6 carbon atoms or $R^{12}$ and $R^{13}$ taken together are an alkylene chain of 3 to 6 carbon atoms; and a or b is a double bond or a single bond, provided that both are not double bonds.

Preferred compounds useful in the present invention include those compounds of Formula (II) wherein:

X is C(O), CHOH or O;

m is 0;

n and are 1;

$R^3$-$R^5$ are H; and/or

Ar is phenyl optionally substituted with halogen, $OCH_3$, $NH_2$, $NO_2$ or another phenyl group.

Specifically preferred compounds useful in the present invention are:

(a) 1-(cyclopropylmethyl)-4-(2'-(4''-fluorophenyl)-2'-oxoethyl) piperidine (b) 1-(cyclopropylmethyl)-4-(2'-(4''-fluorophenyl)-2'-oxoethyl) piperidine, hydrobromide salt (c) 1-(cyclopropylmethyl)-4-(2'-(4''-chlorophenyl)-2'-oxoethyl) piperidine (d) 1-(cyclopropylmethyl)-4-(2'-(4''-chlorophenyl)-2'-oxoethyl) piperidine, hydrobromide salt (e) 1-(cyclopropylmethyl)-4-(4'-fluorophenoxymethyl)-piperidine (f) 1-(cyclopropylmethyl)-4-(4'-fluorophenoxymethyl)-piperidine, hydrochloride salt (g) 1-(cyclopropylmethyl)-4-(4'-chlorophenoxymethyl)piperidine (h) 1-(cyclopropylmethyl)-4-(4'-chlorophenoxymethyl)piperidine, hydrochloride salt (i) 1-(cyclopropylmethyl)-4-(4'-nitrophenoxymethyl)-piperidine (j) 1-(cyclopropylmethyl)-4-(2'-(4''-biphenyl)-2'-oxoethyl)piperidine (k) 1-(cyclopropylmethyl)-4-(2'-(4''-biphenyl)-2'-oxoethyl)piperidine, hydrobromide salt.

Pharmaceutical compositions comprising an effective amount of a compound of Formula I or II and a pharmaceutically acceptable carrier are useful in the method of the present invention.

The preparation of the (N-phthalimidoalkyl) piperidine compounds of Formula I is described in copending, commonly assigned U.S. patent application U.S. Ser. No. 07/570,199, filed 8/20/90, the disclosure of which is hereby incorporated by reference. The compound referred to herein as Ex. No. 504 is designated as the compound of Example No. 504 in U.S. Ser. No. 07/570,199.

The preparation of the 1-cycloalkyl piperidine compounds of Formula II is described in copending, commonly assigned U.S. patent application U.S. Ser. No. 07/602,024, filed 10/23/90, the disclosure of which is hereby incorporated by reference. The compound referred to herein as Ex. No. 3 is referred to as Example No. 3 in U.S. Ser. No. 07/428,097.

Other sigma receptor antagonists lacking or having relatively weak dopamine receptor blocking activity are expected to have similar medical and social benefits for the treatment of cocaine according to the present invention. Examples of other sigma receptor antagonists lacking or having weak domamine receptor blocking activity and expected to be useful for the treatment of cocaine abuse are rimcazole (also known as BW234U) (Ferris et al. (1982) J. Pharm. Pharmacol. 34: 388–390; Ferris et al. (1986) Life Sciences 38: 2329–2337; U.S. Pat. No. 4,400,383; U.S. Pat. No. 4,588,728), remoxipride (Ogren et al. (1984) European Journal of Pharmacology 102: 439–474; U.S. Pat. No. 4,232,037; Snyder and Largent (1989) J. Neuropsychiatry 1: 7–15), and BMY14802 (Taylor and Dekleva (1987) Drug Development Research 11: 65–70; U.S. Pat. No. 4,605,655). The above identified patents are hereby incorporated by reference.

Other sigma receptor antagonists lacking or having relatively weak dopamine receptor blocking activity and expected to be useful in the method of the invention include the compounds of copending, commonly assigned U.S. patent applications U.S. Ser. No. 07/506,961, filed 3/28/90 and U.S. Ser. No. 07/500,573, filed 3/28/90, the disclosures of which are hereby incorporated by reference.

EXAMPLE 1

Cocaine was administered to mice or rats and its effect in stimulating motor activity was quantified. The cocaine-stimulated motor activity was used to evaluate the effects of the sigma receptor antagonist in reducing this enhanced motor stimulation, i.e., counteracting the pharmacological effect of cocaine in the animal.

Figure 1:
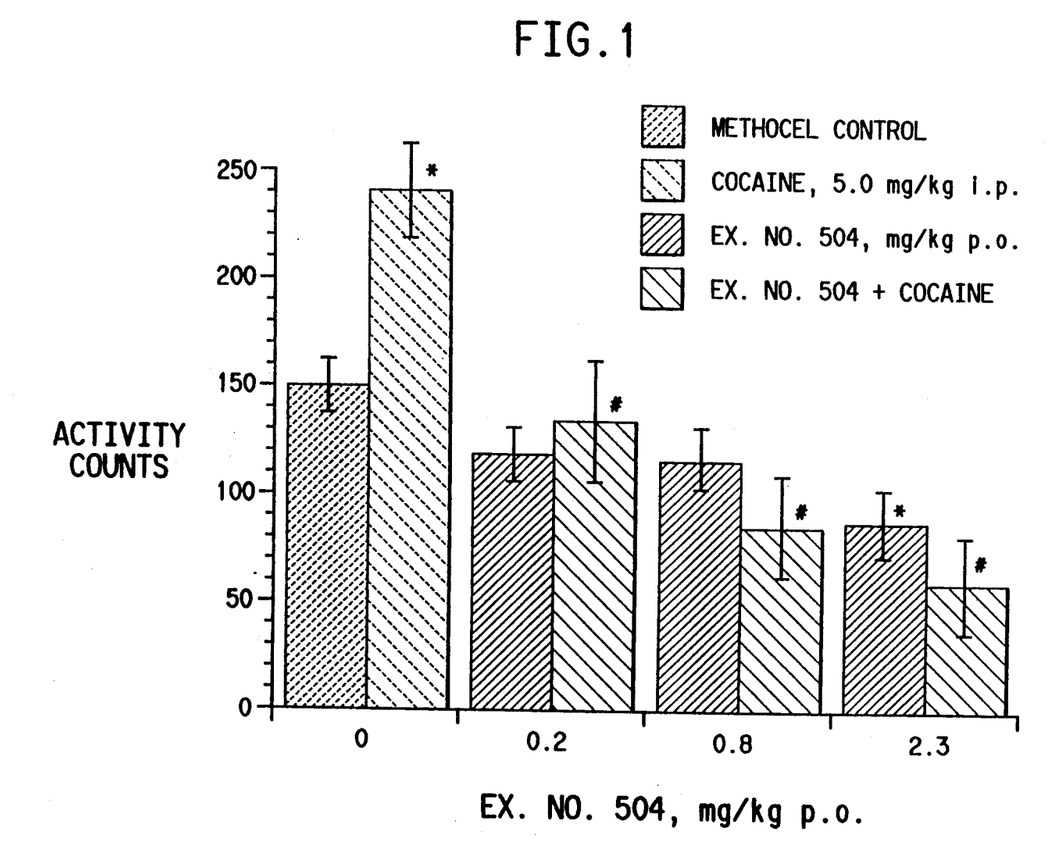
FIG. 1 shows the effect of Ex. No. 504 on cocaine-stimulated confinement motor activity in mice. The same data is also shown in table format in Table 1.
Figure 2:
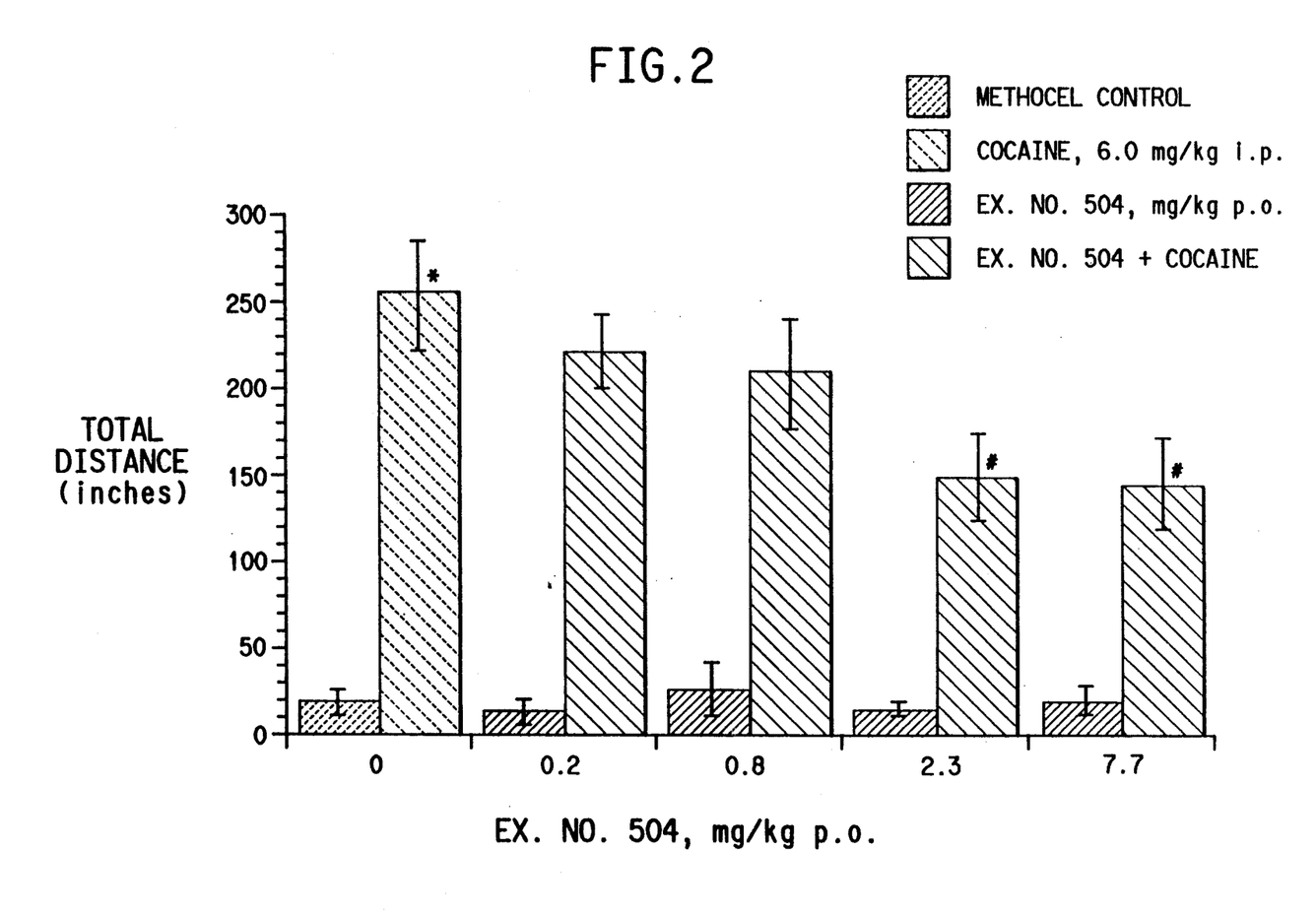
FIG. 2 shows the effect of Ex. No. 504 on cocaine stimulated locomotor activity in rats. The same data is also shown in table format in Table 2.

A representative sigma receptor antagonist lacking or having weak dopamine receptor-blocking activity, Ex. No. 504, reduced the cocaine-induced increases in motor activity in both mice and rats. Ex. No. 504 was effective at doses which were not depressant on the baseline motor activity in control animals not administered with cocaine (Table 1 & FIG. 1) (Table 2 & FIG. 2).

TABLE 1

Effect of Ex. No. 504 on Cocaine-stimulated Confinement Motor Activity in Mice

| Treatment | | Methocel | [Ex. No. 504] (mg/kg, po) | | |
|---|---|---|---|---|---|
| | | | 0.2 | 0.8 | 2.3 |
| +Saline, i.p. | N | 47 | 16 | 16 | 15 |
| | Mean | 149 | 119 | 116 | 88* |
| | SEM | 12 | 13 | 16 | 16 |
| +Cocaine, | N | 16 | 8 | 7 | 8 |
| 5.0 mg/kg i.p. | Mean | 239* | 134# | 86# | 59*# |
| | SEM | 32 | 41 | 31 | 23 |

Animals were administered with Ex. No. 504 at 15 min prior to cocaine administration and the start of a 60 min recording session. Data was analyzed by ANOVA and Dunnett's T Test. *: $p < .05$ from methocel control; #: $p < .05$ from cocaine control.

Animals were administered with Ex. No. 504 at 15 min prior to cocaine administration and the start of a 60 min recording session. Data was analyzed by ANOVA and Dunnett's T Test. *: p>0.05 from methocel control; #: p>0.05 from cocaine control.

TABLE 2

Effect of Ex. No. 504 on Cocaine-stimulated Locomotor Activity in Rats

| Treatment | | Saline | [Ex. No. 504] (mg/kg, po) | | | |
|---|---|---|---|---|---|---|
| | | | 0.2 | 0.8 | 2.3 | 7.7 |
| +Saline, i.p. | N | 16 | 8 | 7 | 16 | 8 |
| | Mean | 17 | 15 | 24 | 13 | 17 |
| | SEM | 9 | 9 | 18 | 6 | 10 |
| +Cocaine, | N | 26 | 8 | 8 | 16 | 19 |
| 6.0 mg/kg i.p. | Mean | 254* | 218* | 211* | 151*# | 145*# |
| | SEM | 33 | 22 | 40 | 25 | 26 |

Animals were administered with Ex. No. 504 at 15 min prior to cocaine administration and the start of a 60 min session. Activity was monitored for a 30 min period beginning 30 min after the rats were placed in the cages. Data was analyzed by ANOVA and Dunnett's T-Test. *: $p < .05$ from saline control; #: $p < .05$ from cocaine control. Ex. No. 504 was not significantly different from methocel control.

In contrast, we have found in the same animal system that the neuroleptic haloperidol, which antagonizes both sigma and dopamine receptors, did not specifically inhibit cocaine-induced behavior and significantly depressed baseline motor activity in the absence of cocaine.

These findings indicate that Ex. No. 504 and other sigma receptor antagonists lacking or having relatively weak dopamine receptor-blocking activity may be useful as selective medications for cocaine abuse problems and other situations where attenuation of the effects of cocaine with minimum adverse neurological effects would be of medical or social benefit.

Animals

Male CF-1 mice weighing 20-22 grams and CDF rats weighing 200 to 250 grams (Charles River Breeding Laboratories, Kingston, NY) were used. Mice were housed 12 and rats 2 per clear plastic cage (47L×26W×16H cm) with Alpha-Dri bedding, in a temperature regulated room (22° C.), under a normal light-dark cycle, with ad-lib food and water. At least 7 days acclamation to the animal facility was allowed.

Apparatus

In mice, activity was measured in a confined area using 64 isolated plexiglas chambers (9L×8W×31H cm) with an infrared photocell beam 9 cm above the table top, one mouse was placed in each chamber. Each chamber was visually isolated by black plexiglas. Experiments were conducted under normal laboratory illumination. Vertical movement was detected by photocell beam breaks and collected with a Cromemco computer. In rats, activity was measured in a relatively larger area using 8 Digiscan Animal Activity Monitors (16.5L×16.5L×12H inches; Omnitech Electronics, Inc.). One rat was placed in each chamber. The monitors were visually isolated from each other. Experiments were conducted in the dark. Total distance traveled (in inches) was the activity measure used.

Procedure

Mice were fasted overnight brought to the lab and grouped according to treatment approximately 3 hours before injection. Rats were fasted overnight and brought to the lab approximately 1 hour before treatment. Mice and rats were treated with Ex. No. 504 at 15 minutes before treatment with cocaine after which the animals were placed into the activity chambers. For mice, activity was recorded for 1 hour beginning immediately after cocaine (5.0 mg/kg, i.p.) administration. For rats, activity was recorded for 30 min beginning 30 min after cocaine (6.0 mg/kg, i.p.) administration.

Dosage Forms

Daily dosage ranges from 1 mg to 2000 mg. Dosage forms (compositions) suitable for administration ordinarily will contain 0.5-95% by weight of the active ingredient based on the total weight of the composition.

The active ingredient can be administered orally in solid dosage forms, such as capsules, tablets, and powders, or in liquid dosage forms, such as elixirs, syrups, and suspensions; it can also be administered parenterally in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences,* Mack Publishing Co., a standard reference text in this field.

What is claimed is:

1. A method of treating cocaine abuse or addiction by attenuating the pharmacological effects of cocaine in a mammal which comprises administering to the mammal in need of such treatment an effective amount of a sigma receptor antagonist lacking or having relatively weak dopamine receptor-blocking activity, to reduce the pharmacological effects of the cocaine.

2. A method of claim 1 wherein the sigma receptor antagonist has an inhibition constant $K_i$ for sigma receptors of at least 500 nM and has at least a 5-fold greater affinity for sigma receptors relative to dopamine receptors.

3. A method of claim 1 wherein the sigma receptor antagonist has an inhibition constant $K_i$ for sigma receptors of at least 500 nM and has at least a 10-fold greater affinity for sigma receptors relative to dopamine receptors.

4. A method of claim 1 wherein the sigma receptor antagonist has an inhibition constant $K_i$ for sigma receptors of at least 500 nM and has at least a 50-fold greater affinity for sigma receptors relative to dopamine receptors.

5. A method of claim 1 wherein the sigma receptor antagonist has an inhibition constant $K_i$ for sigma receptors of at least 500 nM and has at least a 100-fold greater affinity for sigma receptors relative to dopamine receptors.

6. A method of claim 1 wherein the sigma receptor antagonist has an inhibition constant $K_i$ for sigma receptors of at least 100 nM and has at least a 5-fold greater affinity for sigma receptors relative to dopamine receptors.

7. A method of claim 1 wherein the sigma receptor antagonist has an inhibition constant $K_i$ for sigma receptors of at least 100 nM and has at least a 10-fold greater affinity for sigma receptors relative to dopamine receptors.

8. A method of claim 1 wherein the sigma receptor antagonist has an inhibition constant $K_i$ for sigma receptors of at least 100 nM and has at least a 50-fold greater affinity for sigma receptors relative to dopamine receptors.

9. A method of claim 1 wherein the sigma receptor antagonist has an inhibition constant $K_i$ for sigma receptors of at least 100 nM and has at least a 100-fold greater affinity for sigma receptors relative to dopamine receptors.

10. A method according to claim 1 wherein the sigma receptor antagonist is selected from the group consisting of BMY14802, rimcazole, and remoxipride.

11. A method of claim 1, wherein the sigma receptor antagonist is a compound having the formula:

(I)

or a pharmaceutically acceptable salt or an N-oxide thereof wherein:

a is a single or double bond, provided that when a is a double bond then $R^2(CH_2)_n$ is attached at C-4;

n is 0–4, provided that when $(CH_2)_nR^2$ is attached to the 2-position of the piperidine ring then n is 2–4;

$R^1$ is $(CH_2)_mR^3$ or $(CH_2)_pAr$, where m is 1–4 and p is 1–4;

$R^2$ is

R³ is cycloalkyl of 3 to 8 carbon atoms;
R⁴ is 1–4 substituents independently selected from the group consisting of H, halogen, NO₂, NH₂, haloalkyl of 1 to 3 carbon atoms and 1 to 7 halogen atoms, $C_1$–$C_3$ alkyl, NHCOR⁷, NHCO-phenyl, OH, OR⁸ and Ar′;
R⁵ and R⁶ independently are H, alkyl of 1 to 3 carbon atoms, Ar″ or taken together are —CH=CH—CH=CH—;
R⁷ and R⁸ independently are H or alkyl of 1 to 3 carbon atoms;
X is O; H₂; H, OH, R⁹, OH; Ar‴, OH; H, R⁹; or H, OR⁹;
Y is CH₂, CHR¹⁰, C(R¹⁰)₂, O, CH₂CH₂, (CH₂)₃, Ar′, Ar″ and Ar‴ independently are phenyl optionally substituted with 1–5 substituents independently selected from the group consisting of: H, halogen, OH, alkoxy of 1 to 3 carbon atoms, NR¹¹R¹², SH, S(O)$_t$R¹³, where t is 0–2, haloalkyl of 1 to 3 carbon atoms and 1 to 7 halogen atoms, alkyl of 1 to 3 carbon atoms, CO₂H, carboalkoxy of 2 to 6 carbon atoms, CN, NO₂, SO₂NH₂, SO₃H, CO₂NR¹⁴R¹⁵, naphthyl, pyridyl, pyrimidyl, quinolyl or isoquinolyl; atoms;
R⁹–R¹⁰ independently are alkyl of 1 to 3 carbon atoms;
R¹¹–R¹⁵ independently are H or alkyl of 1 to 3 carbon atoms;
R¹⁶ is H; OH; O-alkyl of 1–6 carbons; O-acyl of 1–8 carbons; alkyl of 1–12 carbons; phenyl substituted with one or two substituents independently selected from F, Cl, Br, I, alkyl, perfluoroalkyl, alkoxy, arylosy, alkylthio, arylthio, perfluoroalkoxy, perfluoroalkylthio, and dialkylamino (alkyl and alkoxy 1–12 carbons; aryl 6–12 carbons); 1- and 2-naphthyl substituted with one or two substituents independently selected from F, Cl, Br, I, alkyl, perfluoroalkyl, alkoxy, arylosy, alkylthio, arylthio, perfluoroalkoxy, perfluoroalkylthio, and dialkylamino (alkyl and alkoxy 1–12 carbons; aryl 6–12 carbons); 2- and 3-pyrrolyl; 2- and 3- furyl; 2- and 3- thienyl; 2,3, and 4-pyridyl; 2- and 3-benzolfuryl; 2- and 3- indolyl; 2- and 3-benzothienyl; 2, 3, and 4- quinolyl; and 1, 3, and 4-isoquinolyl;
provided however that:
(1) when R¹ is (CH₂)$_p$Ar (where p is 1); R² is and

(CH$_2$)$_n$R$^2$, (n=0), is attached at the C-4 position on the piperidine ring; then X cannot be H$_2$ or O.

(2) R$^{16}$ is H, OH, alkyl or aryl when (CH$_2$)$_n$R$^2$ is attached to the 4-position of the piperidine ring.

12. A method of claim 11 wherein n is 1–4.
13. A method of claim 11 wherein R$^1$ is (CH$_2$)$_p$Ar.
14. A method of claim 11 wherein R$^2$ is selected from the group consisting of or where X, Y, R$^4$, R$^5$ and R$^6$ are as defined in claim 15. A method of claim 11 wherein (CH$_2$)nR$^2$ is attached at the C-4 position of the piperidine ring.
16. A method of claim 11 wherein X is O or H$_2$.
17. A method of claim 11 wherein R$^4$, R$^5$ and R$^6$ are all H.
18. A method of claim 11 wherein p is 1 or 2.
19. A method of claim 11 wherein Ar is phenyl.
20. A method of claim 11 wherein Y is (CH$_2$)$_3$ or O.
21. A method of claim 11 wherein:
n is 1–4;
R$^1$ is (CH$_2$)$_p$Ar;
p is 1-2;

or (CH$_2$)$_n$R$^2$ is attached at the C-4 position of the piperidine ring; and/or

X is O or H$_2$;
R$^4$, R$^5$ and R$^6$ are all H;
Ar is phenyl;
Y is (CH$_2$)$_3$ or O.

22. A method of claim 21 wherein:
n is 1;
R$^2$ is

X is O; and
p is 2.

23. A method of claim 21 wherein:
n is 1;
R$^2$ is

X is O;
Y is (CH$_2$)$_3$; and
p is 2.

24. A method of claim 21 wherein:
n is 1;
R$^2$ is

X is O;
Y is O; and
p is 2.

25. A method of claim 21 wherein:
n is 1;
R$^2$ is

X is H$_2$; and
p is 2.

26. A method of claim 1 wherein the sigma receptor antagonist is a compound having the formula:

(II)

or a pharmaceutically acceptable salt thereof, wherein:
m is 0 to 3;
n is 0 to 3;
provided that m and n are not both 0;
p is 0 to 3;
X is O, S, SO, $SO_2$, $NR_6$, $CR^7R^8$ or CHOH;
$R^1$, $R^3$ and $R^7$ independently are H, alkyl of 1 to 5 carbon atoms, halogen, $NR^{10}R^{11}$, OH, $CO_2H$, carboalkoxy of 2 to 6 carbon atoms, CN, $Ar^1$, alkoxy of 1 to 5 carbon atoms or alkylthio of 1 to 5 carbon atoms;
$R^2$, $R^4$ and $R^8$ independently are H, alkyl of 1 to 5 carbon atoms, carboalkoxy of 2 to 6 carbon atoms, CN, alkoxy of 1 to 5 carbon atoms or $Ar^1$;
provided that $R^1$, $R^2$, $R^3$ and $R^4$ are not alkoxy of 1 to 5 carbon atoms, alkylthio of 1 to 5 carbon atoms, $NR^{10}R^{11}$ or OH when X is O, S, SO, $SO_2$ or $NR^6$;
$R^5$ is H, alkyl, halogen, OH or alkenyl;
$R^6$ is H, alkyl of 1 to 5 carbon atoms or $Ar^1$;
Ar and $Ar^1$ independently are naphthyl, pyridyl, pyrimidyl, indolyl, quinolinyl, isoquinolinyl, or phenyl optionally substituted with alkyl of 1 to 3 carbon atoms, alkoxy of 1 to 3 carbon atoms, haloalkyl of 1 to 3 carbon atoms and 1 to 7 halogen atoms, SH, S(0)t alkyl of 1 to 3 carbon atoms, where t is 1, 2 or 3, dialkylamino of 2 to 6 carbon atoms, halogen, OH, alkylamino of 1 to 3 carbon atoms, $NH_2$, CN, $NO_2$, $SO_3H$, tetrazole, $CO_2H$, carboalkoxy of 2 to 6 carbon atoms, $CONH_2$, $SO_2NH_2$, $COR^9$, $CONR^{12}R^{13}$, $SO_2NR_{12}R^{13}$, $Ar^2$, $OAr^2$ or $SAr^2$;
$Ar^2$ is naphthyl or phenyl optionally substituted with alkyl of 1 to 3 carbon atoms, haloalkyl of 1 to 3 carbon atoms and 1 to 7 halogen atoms, alkoxy of 1 to 3 carbon atoms, halogen or alkylthio of 1 to 3 carbon atoms;
$R^9$, $R^{10}$, $R^{11}$, $R^{12}$ and $R^{13}$ independently are H, alkyl of 1 to 5 carbon atoms or phenyl or $R^{10}$ and $R^{11}$ taken together are an alkylene chain of 3 to 6 carbon atoms or $R^{12}$ and $R^{13}$ taken together are an alkylene chain of 3 to 6 carbon atoms; and
a or b is a double bond or a single bond, provided that both are not double bonds.

27. A method of claim 26 wherein:
X is CO, CHOH or O;
m is 0;
n and p are 1;
$R^3$–$R^5$ are H; and/or
Ar is phenyl optionally substituted with halogen, $OCH_3$, $NH_2$, $NO_2$ or another phenyl group.

28. A method according to claim 26 wherein the compound is 1-(cyclopropylmethyl)-4-(2'-(4''-fluorophenyl)-2'-oxoethyl) piperidine.

29. A method according to claim 26 wherein the compound is 1-(cyclopropylmethyl)-4-(2'-(4''-chlorophenyl)-2'-oxoethyl) piperidine.

30. A method according to claim 26 wherein the compound is 1-(cyclopropylmethyl)-4-(4'-fluorophenoxymethyl) piperidine.

31. A method according to claim 26 wherein the compound is 1-(cyclopropylmethyl)-4-(4'-chlorophenoxymethyl)piperidine.

32. A method according to claim 26 wherein the compound is 1-(cyclopropylmethyl)-4-(4'-nitrophenoxymethyl) piperidine.

33. A method according to claim 26 wherein the compound is 1-(cyclopropylmethyl)-4-(2'-(4''-biphenyl)-2'-oxoethyl)piperidine.

* * * * *